United States Patent [19]
Valyocsik

[11] Patent Number: 5,614,629
[45] Date of Patent: Mar. 25, 1997

[54] BENZYL QUATERNARY TROPINIUM COMPOUND

[75] Inventor: Ernest W. Valyocsik, Yardley, Pa.

[73] Assignee: Mobil Oil Corporation, Fairfax, Va.

[21] Appl. No.: 380,278

[22] Filed: Jan. 30, 1995

[51] Int. Cl.$^6$ .................. C07D 451/02; C07D 453/02
[52] U.S. Cl. .................................. 546/124; 546/133
[58] Field of Search ................................ 546/133, 124

[56] References Cited

U.S. PATENT DOCUMENTS 4,531,967  7/1985  Van Heertum et al. .............. 504/246

Primary Examiner—Alan L. Rotman
Attorney, Agent, or Firm—Peter W. Roberts; Malcolm D. Keen

[57] ABSTRACT

This invention is directed to novel benzyl quaternary ammonium compounds and their synthesis. The compounds have valuable utility as organic directing agents in the crystallization of a silicate structure which, in turn, is useful as a catalyst component, sorbent, and/or ion-exchanger. More particularly, this invention is concerned with benzyl quaternary ammonium compounds synthesized by selective alkylation of the bridgehead nitrogen of tropane or quinuclidine with a benzyl salt.

5 Claims, 2 Drawing Sheets

BENZYL QUATERNARY TROPINIUM COMPOUND

FIELD OF THE INVENTION

This invention is directed to novel benzyl quaternary ammonium compounds and their synthesis. The compounds of this invention are novel compounds having valuable utility as organic directing agents in the crystallization of a silicate structure, which, in turn, is useful as a catalyst component, sorbent, and/or ion-exchanger. More particularly, this invention is concerned with benzyl quaternary ammonium compounds conveniently and reproducibly synthesized by reaction of a readily available benzyl salt with either quinuclidine or tropane.

DESCRIPTION OF THE PRIOR ART

Tropane, or 8-methyl-8-azabicyclo[3.2.1]octane, having the formula

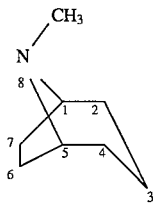

is a known compound detailed in *The Merck Index,* 10th ed., No. 9580. A number of substituted derivatives of tropane are also detailed in *The Merck Index,* 10th ed., as follows.

tropine, No. 9586, tropentane, No. 9582, tropeine, No. 9581, tropine benzylate, No. 9587, tropacine, No. 9576, tropacocaine, No. 9577, and atropine, No. 878.

Tropine, or endo-8-methyl-8-azabicyclo[3.2.1]octan-3-ol, having the formula

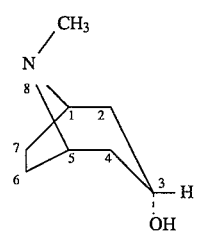

can be prepared as in U.S. Pat. Nos. 2,366,760 and 2,746,976, incorporated herein by reference.

Tropentane, or 1-phenylcyclopentanecarboxylic acid 8-methyl-8-azabicyclo[3.2.1]oct-3-yl ester, having the formula

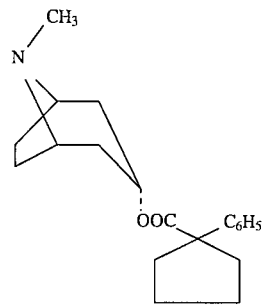

is prepared from tropine and 1-phenylcyclopentanecarboxyl chloride.

Tropeine is a name given to esters of tropine in general, while tropine benzylate, or endo-α-hydroxy-α-phenylbenzene-acetic acid 8-methyl-8-azabicyclo[3.2.1]oct-3-yl ester, has the formula

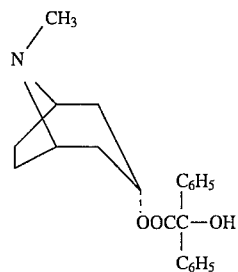

Tropacine, or endo-α-phenylbenzeneacetic acid 8-methyl-8-azabicyclo[3.2.1]oct-3-yl ester, having the formula

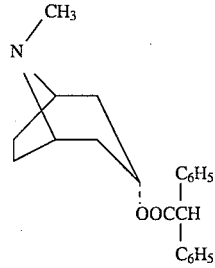

is prepared from tropine and diphenylacetyl chloride as in Swiss Patent 202,181, incorporated herein by reference.

Tropacocaine, or exo-8-methyl-8-azabicyclo[3.2.1]octan-3-ol benzoate having the formula

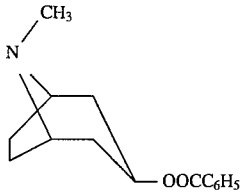
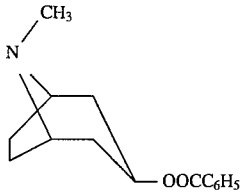

is prepared by heating pseudotropine with water and benzoic anhydride.

Atropine, or endo-(±)-α-(hydroxymethyl)benzeneacetic acid 8-methyl-8-azabicyclo[3.2.1]oct-3-yl ester, has the formula

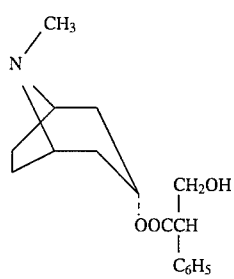

Quinuclidine, or 1-azabicyclo[2.2.1]octane, has the formula

SUMMARY OF THE INVENTION

This invention provides novel benzyl quaternary ammonium compounds having the formula

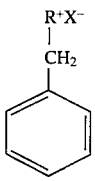

wherein R is

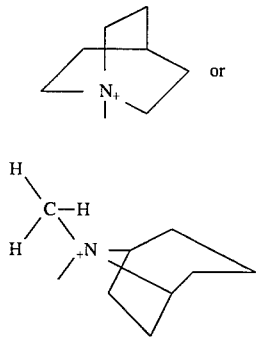

and X is an anion selected from the group consisting of halide (e.g., iodide, chloride, or bromide); hydroxide; nitrate; sulfate; perchlorate; and bisulfate. Synthesis of said compound by reaction of a benzyl salt with either quinuclidine or tropane is also provided.

EMBODIMENTS

Figure 1:
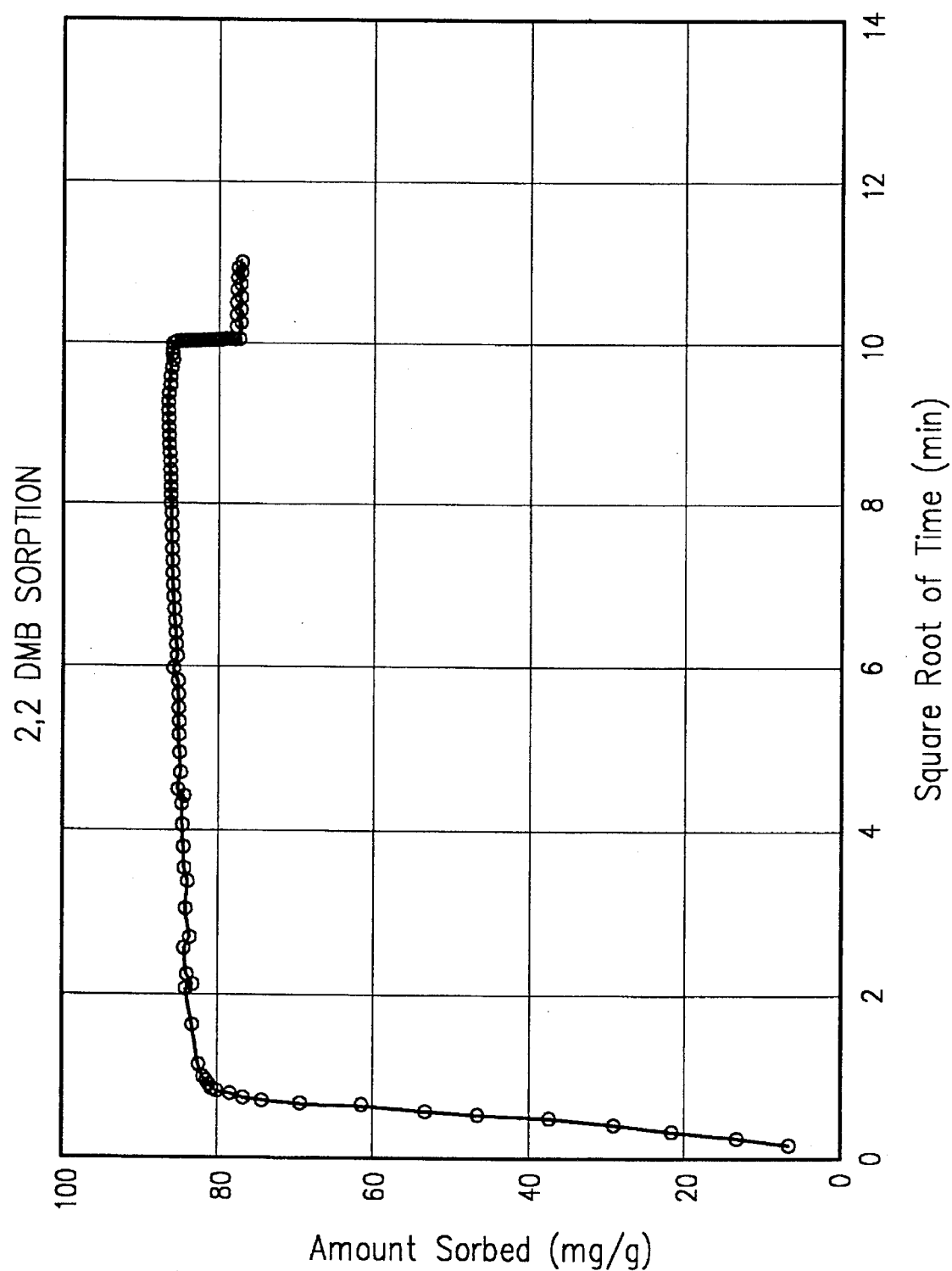
FIG. 1 shows 2,2-dimethylbutane sorption measurements obtained for Example 19.

As will be noted from the above formula for the benzyl quaternary ammonium compounds of this invention, the present compounds are synthesized by alkylation selectively at the bridgehead nitrogen of the starting material compound, selected from the group consisting of tropane and quinuclidine, with a benzyl salt, such as, for example, benzyl halide. This reaction is conducted in a suitable solvent, such as, for example an alcohol of from 1 to about 8 carbon atoms, e.g., ethanol. The starting material compounds must be soluble in the solvent chosen.

The compounds of this invention are benzylquinuclidinium and benzyltropanium compounds, such as, for example, the halide, hydroxide, nitrate, sulfate, perchlorate, or bisulfate.

The synthesis method utilized for preparation of the compounds of this invention involves contacting the appropriate starting material compounds in a suitable solvent medium at alkylation reaction conditions including a temperature of from about ambient to reflux, and a pressure of from atmospheric to about 500 psig, preferably about atmospheric. The time required for the reaction will, of course, depend upon such factors as temperature and pressure, as well as relative concentrations of reactants and desired degree of reaction, but usually will be from about 10 hours to about 4 days.

The reflux temperature of reaction limitation will depend upon the amount and nature of solvent used. Generally, the reaction mixture will comprise tropane or quinuclidine and alkylating agent benzyl salt in the mole ratio of from about 0.75 to about 1.25 moles alkylating agent/mole tropane or quinuclidine, and from about 5 to about 10 moles solvent.

A suitable solvent, preferably polar, may be used in the reaction. Such solvents include an alcohol of from 1 to about 8 carbon atoms, ether of from 2 to about 10 carbon atoms, or combinations thereof, especially methanol, ethanol, acetone, and/or diethyl ether. The tropane or quinuclidine must be soluble in the solvent chosen to at least about 90 percent. The preferred solvent will be essentially water-free, as will the reaction mixture in which the present compounds are produced. Choice of solvent will determine to a substantial degree the reflux temperature limitation at which the reaction will proceed to a product benzyl quaternary ammonium compound. For example, a solvent of ethanol will determine reflux temperature of about 70° C. Methanol solvent will establish the reflux temperature at about 65° C.

Compounds of the present invention are useful as directing agents in the synthesis of crystalline silicate. Such silicate is useful as a catalyst component, sorbent, and/or ion-exchanger. Such silicate is prepared from a reaction mixture containing sources of an alkali or alkaline earth metal oxide, an oxide of aluminum, an oxide of silicon, water, and the directing agent compound, as is exemplified hereinafter. Such reaction mixture will have a composition, in terms of mole ratios of oxides, within the following ranges:

| | |
|---|---|
| $SiO_2/Al_2O_3$ | 15 to 1000 |
| $H_2O/SiO_2$ | 5 to 200 |
| $OH^-/SiO_2$ | 0 to 3 |
| $M/SiO_2$ | 0 to 3 |
| $R*/SiO_2$ | 0.02 to 1.0 | wherein R* is the cation of the directing agent compound of this invention and M is the alkali or alkaline earth metal cation.

Crystallization of the silicate can be carried out at either static or stirred condition in a suitable reactor vessel, such as, for example, polypropylene jars of teflon-lined or stainless steel autoclaves. The total useful range of temperatures of the silicate crystallization is from about 80° C. to about 250° C. for a time sufficient for crystallization to occur at the temperature used, e.g., from about 12 hours to about 100 days. Thereafter, the crystals are separated from the liquid and recovered. The reaction mixture can be prepared utilizing materials which supply the appropriate oxides. Such materials may include sodium silicate, silica hydrosol, silica gel, silicic acid, sodium hydroxide, a source of aluminum, and the directing agent compound.

It should be realized that the reaction mixture oxides can be supplied by more than one source. The reaction mixture can be prepared either batchwise or continuously. Crystal size and crystallization time of the crystalline silicate material will vary with the nature of the reaction mixture employed and the crystallization conditions.

The following examples illustrate the present invention.

EXAMPLE 1

Benzylquinuclidinium halide, i.e., bromide, was synthesized by reacting benzylbromide and quinuclidine in absolute ethanol solvent in a flask equipped with a reflux condenser, a thermometer and a stirrer. The flask was charged with 60.0 grams of benzylbromide with 200 ml of absolute ethanol. Then 33.4 grams of quinuclidine dissolved in 300 ml of absolute ethanol was transferred to the flask. Heating and stirring of the flask reaction mixture commenced immediately.

The reaction mixture was refluxed (~70° C.) overnight with 15 stirring before quenching the reaction vessel in a dry ice-acetone bath to −40° C. The cold crystalline product was separated from the solvent, filtered, and washed with anhydrous diethylether on a Büchner funnel. The crystals were dried in an air stream, then chemically analyzed. The benzylquinuclidium bromide product of this example was found to be composed of 56.13 wt. % C, 7.46 wt. % H, 4.66 wt. % N and 28.13 wt. % Br.

EXAMPLE 2

Benzyltropanium halide, i.e., bromide, was synthesized by reacting benzylbromide and tropane in absolute ethanol solvent in a flask equipped with a reflux condenser, a thermometer and a stirrer. The flask was charged with 60.0 grams of benzylbromide with 300 ml of absolute ethanol. Then 37.6 grams of tropane dissolved in 300 ml of absolute ethanol 30 was transferred to the flask. Heating and stirring of the flask reaction mixture commenced immediately.

The reaction mixture was refluxed (~70° C) overnight with stirring before quenching the reaction vessel in a dry ice-acetone bath to −40° C. The cold crystalline product was separated from the solvent, filtered, and washed with anhydrous diethylether on a Büchner funnel. The benzyltropanium bromide product crystals were then dried in an air stream.

The following examples show utility of the benzyl quaternary ammonium compounds of this invention as crystallization directing agents in manufacture of synthetic crystalline silicate. In the examples, whenever adsorption data are set forth form comparison of sorptive capacities for 2,2-dimethylbutane (2,2-DMB) and n-hexane, they were Equilibrium Adsorption values as follows.

A weighed sample of the calcined adsorbant was contacted with the desired pure adsorbate vapor in an adsorption chamber, evacuated to less than 1 mm and contacted with 40 Torr of n-hexane or 2,2-DMB vapor, pressures less than the vapor-liquid equilibrium pressure of the respective adsorbate at 30° C. for n-hexane and 90° C. for 2,2-DMB. The pressure was kept constant (within about ±0.5 mm) by addition of adsorbate vapor controlled by a manostat during the adsorption period, which did not exceed about 8 hours.

As adsorbate was adsorbed by the new crystal, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in mg/g of calcined adsorbant.

When Alpha Value is examined, it is noted that the Alpha Value is an approximate indication of the catalytic cracking activity of a catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant =0.016 sec$^{-1}$). The Alpha Test is described in U.S. Pat. No. 3,354,078; in the *Journal of Catalysis*, 4, 527 (1965); 6, 278 (1966); and 61, 395 (1980), each incorporated herein by reference as to that description. The experimental conditions of the test used herein include a constant temperature of 538° C. and a variable flow rate as described in detail in the *Journal of Catalysis*, 61, 395.

When X-ray diffraction data are provided, they were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units (A), and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects.

EXAMPLES 3–13

Experiments were conducted for synthesis of crystalline product material. In these experiments, $Al_2(SO_4)_3 \cdot 18H_2O$ and KOH pellets were dissolved in deionized water. Benzylquinuclidinium bromide prepared in Example 1 above was then dissolved in the solution. Colloidal silica sol (30 wt. % $SiO_2$) was then mixed into the solution. The mixture was stirred for 2 minutes to produce a uniform, fluid hydrogel, having, respectively, the compositions shown in Table I where R* is the cation of benzylquinuclidinium bromide.

The hydrogel of each experiment was then transferred to a 300 ml stainless steel autoclave equipped with a stirrer. The autoclave was capped and sealed; and 400 psig of inert gas was introduced into the autoclave. Stirring and heating were started immediately. Crystallizations were carried out at 170° C. with stirring.

Crystalline products were recovered, filtered, washed with deionized water, and dried on a filter funnel in an air 20 stream under an infrared lamp. The dried crystalline powder products were then submitted for X-ray diffraction and chemical analysis.

TABLE I

| | Mixture Composition (mole ratios)[1] | | | |
|---|---|---|---|---|
| Example | $SiO_2/Al_2O_3$ | $K^+/SiO_2$ | Reaction time, days | Product |
| 3 | 10 | 1.10 | 7 | Zeolite |
| 4 | 25 | 0.62 | 7 | Zeolite mixture |
| 5 | 30 | 0.57 | 7 | Zeolite |
| 6 | 30 | 0.57 | 2 | Zeolite |
| 7 | 30 | 0.57 | 7 | Zeolite |
| 8 | 30 | 0.57 | 7 | Zeolite |

TABLE I-continued

| Example | Mixture Composition (mole ratios)[1] | | | Product |
|---|---|---|---|---|
| | $SiO_2/Al_2O_3$ | $K^+/SiO_2$ | Reaction time, days | |
| 9 | 30 | 0.57 | 3 | Zeolite |
| 10 | 60 | 0.43 | 7 | Zeolite |
| 11 | 60 | 0.43 | 7 | Zeolite |
| 12 | 70 | 0.41 | 7 | Zeolite |
| 13 | 180 | 0.34 | 7 | Zeolite + α-quartz |

[1]$H_2O/SiO_2 = 40$, $OH^-/SiO_2 = 0.30$, $R^*/SiO_2 = 0.20$

The X-ray diffraction data for the as-synthesized products of Examples 8 and 9 are presented in Tables II and III, respectively.

TABLE II

| Interplanar d-Spacing (A) | $I/I_o$ |
|---|---|
| 10.87 | 95 |
| 9.18 | 7 |
| 6.55 | 14 |
| 5.86 | 6 |
| 5.57 | 5 |
| 5.43 | 12 |
| 5.02 | 1 |
| 4.68 | 26 |
| 4.59 | 5 |
| 4.35 | 100 |
| 4.23 | <1 |
| 4.17 | 31 |
| 4.12 | 54 |
| 3.94* | <1* |
| 3.77 | 40 |
| 3.69 | 1 |
| 3.61 | 11 |
| 3.54 | 6 |
| 3.43 | 39 |
| 3.37 | 27 |
| 3.32* | 5* |
| 3.28 | 6 |
| 3.25 | 7 |
| 3.22 | 2 |
| 3.18 | 8 |
| 3.12 | 2 |
| 3.06 | 11 |
| 2.99 | 3 |
| 2.930 | 2 |
| 2.886 | 1 |
| 2.844 | 6 |
| 2.814 | <1 |
| 2.788 | 3 |
| 2.715 | 3 |
| 2.660 | 5 |
| 2.605 | 3 |
| 2.561 | 5 |
| 2.537 | 3 |
| 2.511 | 4 |
| 2.464 | 6 |
| 2.173 | 4 |

*Peak attributed to unidentified impurity phase

TABLE III

| Interplanar Spacing (A) | $I/I_o$ |
|---|---|
| 10.91 | 73 |
| 9.21 | 6 |
| 6.57 | 16 |
| 5.87 | 5 |
| 5.58 | 5 |
| 5.43 | 12 |
| 5.03 | 2 |
| 4.97* | <1* |
| 4.69 | 27 |
| 4.59 | 4 |
| 4.36 | 100 |
| 4.23 | 7 |
| 4.17 | 28 |
| 4.13 | 58 |
| 3.95* | 1* |
| 3.77 | 64 |
| 3.70 | 1 |
| 3.61 | 17 |
| 3.55 | 10 |
| 3.44 | 42 |
| 3.37 | 26 |
| 3.33 | 7 |
| 3.30 | 5 |
| 3.29 | 8 |
| 3.26 | 8 |
| 3.22 | 6 |
| 3.18 | 9 |
| 3.12 | 2 |
| 3.07 | 16 |
| 3.00 | 7 |
| 2.934 | 3 |
| 2.889 | 4 |
| 2.845 | 10 |
| 2.816 | 4 |
| 2.790 | 5 |
| 2.716 | 5 |
| 2.661 | 8 |
| 2.607 | 5 |
| 2.561 | 7 |
| 2.536 | 4 |
| 2.513 | 7 |
| 2.464 | 11 |
| 2.173 | 4 |

*Peak attributed to unidentified impurity phase

Chemical analysis results for the as-synthesized products of Examples 4, 5, 7, 8, 10, 11, and 12 are presented in Table IV.

TABLE IV

| Example | Moles C/ Mole N | Moles per Mole $Al_2O_3$ | | | Composition[1] | | |
|---|---|---|---|---|---|---|---|
| | | $N_2O$: | $K_2O$: | $SiO_2$ | Al/ 100 Td | $K^+$/ 100 Td | $R^{*(2)}$/ 100 Td |
| 4 | 17.1 | 0.45 | 0.71 | 20 | 9.0 | 6.4 | 4.1 |
| 5 | 13.0 | 0.83 | 0.18 | 25 | 7.4 | 1.3 | 6.1 |
| 7 | 17.5 | 0.55 | 0.99 | 26 | 7.1 | 7.1 | 3.9 |
| 8 | 17.1 | 0.58 | 0.93 | 24 | 7.7 | 7.1 | 4.5 |
| 10 | 17.0 | 0.64 | 1.36 | 32 | 5.9 | 8.1 | 3.9 |
| 11 | 15.7 | 1.32 | 0.21 | 46 | 4.2 | 0.88 | 5.5 |
| 12 | 17.4 | 1.58 | 0.45 | 66 | 2.9 | 1.3 | 4.6 |

[1]Calculated on the basis of $100(SiO_2 + AlO_2)$ tetrahedra
[2]$R^*$ = benzylquinuclidinium cation There appears to be no clear trend in the alkali metal content per 100 tetrahedra, but there does appear to be approximately 4–6 template cations per 100 tetrahedra in the zeolite framework of the products from examples listed in Table IV, indicating templating activity for the benzylquinuclidinium cation.

EXAMPLES 14–16

Zeolite products of Examples 6, 7, and 8 were weighed into quartz boats, then placed into a Heviduty® tube furnace and sealed with nitrogen gas flowing through the furnace tube. The heating of the furnace was begun at 2° C./minute from room temperature to 538° C. When the furnace reached the maximum temperature, the flowing gas was switched to air, and the calcination of the zeolite was continued for 15 hours before termination.

The air calcined samples were ammonium exchanged with 1M $NH_4NO_3$ at 80° C. for 6 hours. After ammonium exchange, the zeolites were filtered, washed with deionized water, and dried in an air stream on the filter funnel under an infrared heat lamp.

The calcination procedure was repeated on the ammonium-exchanged materials in the tube furnace in the same manner as described above, except this time the samples were held at 538° C. for 8 hours to convert them to the hydrogen form of the zeolite. Examples 14, 15, and 16 products were zeolite materials from the products of Examples 6, 7, and 8, respectively.

EXAMPLE 17

Samples of the hydrogen form product zeolites of Examples 14, 15, and 16 were tested for acid catalytic activity in the Alpha Test and found to have Alpha Values of 521, 164, and 510, respectively.

Constraint Index

A convenient measure of the extent to which a crystalline material provides control to molecules of varying sizes to its internal structure is the Constraint Index (CI) of the material. Zeolites which provide a highly restricted access to and egress from their internal structures have a high value for the Constraint Index, and zeolites of this kind usually have pores of small size, e.g., less than 5 Angstroms. On the other hand, zeolites which provide relatively free access to their internal structures have a low value for the Constraint Index and usually have pores of large size, e.g., greater than 8 Angstroms. The method by which Constraint Index is determined is described fully in U.S. Pat. No. 4,016,218, incorporated herein by reference for details of the method.

Constraint Index values for some typical zeolites are as follows:

| | CI (at test temperature) |
|---|---|
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| MCM-22 | 0.6–1.5 (399° C.–454° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

EXAMPLE 18

The Constraint Index of the hydrogen form product zeolite of Example 15 was determined to be 0.3 at 316° C. This value falls within the classification of the more open structures having 12-membered rings. Hence, it is concluded from the catalytic Constraint Index Test result that the zeolite product of Example 7 contains at least a 12-membered ring structure.

EXAMPLE 19

A sample of the hydrogen form product zeolite of Example 16 was subjected to sorption evaluation. FIG. 1 shows the 2,2-dimethylbutane (2,2-DMB) sorption measurements at 90° C. for this sample. The rapid uptake of 2,2-dimethylbutane indicates a very open pore structure.

EXAMPLE 20

Figure 2:
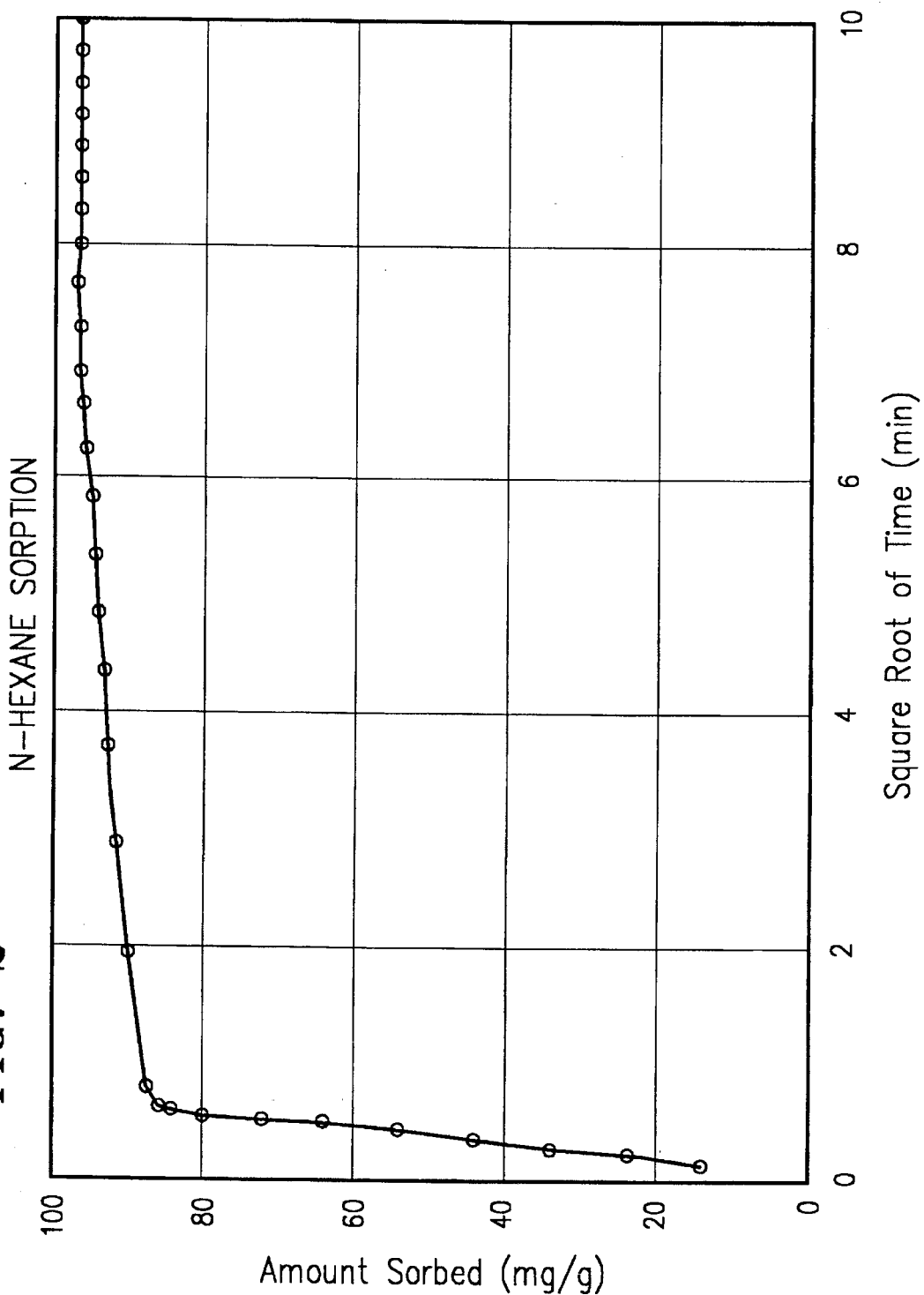
FIG. 2 shows n-hexane sorption measurements obtained for Example 20.

A sample of the hydrogen form product zeolite of Example 16 was also subjected to n-hexane sorption evaluation. FIG. 2 shows the n-hexane sorption measurement at 30° C. for this sample. The rapid uptake of n-hexane indicates a very open structure.

EXAMPLES 21–26

In these experiments, $Al_2(SO_4)_3 \cdot 18H_2O$ and KOH pellets for potassium or NaOH pellets for sodium were dissolved in deionized water. Benzyltropanium bromide prepared in Example 2 above was then dissolved in the solution. Colloidal silica sol (30 wt. % $SiO_2$) was then mixed into the solution. The mixture was stirred for 2 minutes to produce a uniform, fluid hydrogel, having, respectively, the compositions shown in Table V where R* is the cation of benzyltropanium bromide.

The hydrogel of each experiment was then transferred to a 300 ml stainless steel autoclave equipped with a stirrer. The autoclave was capped and sealed; and 400 psig of inert gas was introduced into the autoclave. Stirring and heating were started immediately. Crystallizations were carried out at 170° C with stirring.

Crystalline products were recovered, filtered, washed with deionized water, and dried on a filter funnel in an air stream under an infrared lamp. The dried crystalline powder products were then submitted for X-ray diffraction and chemical analysis.

TABLE V

| | Mixture composition (mole ratios)[1] | | | | |
|---|---|---|---|---|---|
| Example | $SiO_2/$ $Al_2O_3$ | $K^+/$ $SiO_2$ | $Na^+/$ $SiO_2$ | Reaction time, days | Product |
| 21 | 15 | — | 0.44 | 7 | Zeolite |
| 22 | 25 | 0.62 | — | 7 | Zeolite |
| 23 | 30 | — | 0.37 | 7 | Zeolite |
| 24 | 30 | 0.57 | — | 7 | Zeolite |
| 25 | 30 | 0.57 | — | 7 | Zeolite |
| 26 | 30 | 0.57 | — | 7 | Zeolite |

[1]$H_2O/SiO_2 = 40$, $OH^-/SiO_2 = 0.30$, $R^*/SiO_2 = 0.20$

Chemical analysis results for the as-synthesized product of Example 24 is presented in Table VI.

TABLE VI

| Example | Moles C/ Mole N | Moles per Mole Al₂O₃ | | | Composition[1] | | |
| --- | --- | --- | --- | --- | --- | --- | --- |
| | | N₂O | K₂O | SiO₂ | Al/ 100 Td | K⁺/ 100 Td | R*[2]/ 100 Td |
| 24 | 15.6 | 0.93 | 1.5 | 26.3 | 7.1 | 10 | 6.5 |

[1]Calculated on the basis of 100(SiO₂ + AlO₂) tetrahedra
[2]R* = benzyltropanium cation Since there are approximately 6 template cations per 100 tetrahedra in the zeolite framework of the product of Example 24, templating activity for the benzyltropanium cation is indicated.

EXAMPLES 27–29

Zeolite products of Examples 24, 25, and 26 were weighed into quartz boats, then placed into a Heviduty® tube furnace and sealed with nitrogen gas flowing through the furnace tube. The heating of the furnace was begun at 2° C./minute from room temperature to 538° C. When the furnace reached the maximum temperature, the flowing gas was switched to air, and the calcination of the zeolite was continued for 15 hours before termination. Docket 7585

The air calcined samples were ammonium exchanged with 1M NH₄NO₃ at 80° C. for 6 hours. After ammonium exchange, the zeolites were filtered, washed with deionized water, and dried in an air stream on the filter funnel under an infrared heat lamp.

The calcination procedure was repeated on the ammonium-exchanged materials in the tube furnace in the same manner as described above, except this time the samples were held at 538° C. for 8 hours to convert them to the hydrogen form of the zeolite. Examples 27, 28, and 29 products were zeolite materials from the products of Examples 24, 25, and 26, respectively.

What is claimed is:
1. A compound having the formula

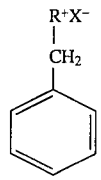

wherein R is

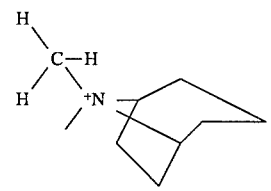

and X is an anion.

2. The compound of claim 1 wherein X is selected from the group consisting of halide, hydroxide, nitrate, perchlorate and bisulfate.
3. The compound of claim 2 wherein X is halide.
4. The compound of claim 1 wherein R is

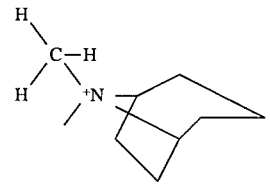

and X is hydroxide or halide selected from the group consisting of chloride, bromide and iodide.
5. The compound of claim 4 wherein X is bromide.

* * * * *